(12) United States Patent
Manjili et al.

(10) Patent No.: US 8,741,642 B2
(45) Date of Patent: Jun. 3, 2014

(54) METHODS FOR PRODUCING AUTOLOGOUS IMMUNE CELLS RESISTANT TO MYELOID-DERIVED SUPPRESSOR CELLS EFFECTS

(75) Inventors: Masoud H. Manjili, Richmond, VA (US); Harry D. Bear, Richmond, VA (US); Maciej Kmieciak, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 13/877,536

(22) PCT Filed: Oct. 21, 2011

(86) PCT No.: PCT/US2011/057195
§ 371 (c)(1),
(2), (4) Date: Apr. 3, 2013

(87) PCT Pub. No.: WO2012/054792
PCT Pub. Date: Apr. 26, 2012

(65) Prior Publication Data
US 2013/0309213 A1 Nov. 21, 2013

Related U.S. Application Data

(60) Provisional application No. 61/405,821, filed on Oct. 22, 2011.

(51) Int. Cl.
*C12N 5/0783* (2010.01)
*C12N 5/0784* (2010.01)
*A61P 35/00* (2006.01)

(52) U.S. Cl.
USPC .................. 435/375; 435/377; 424/93.71

(58) Field of Classification Search
CPC .............. C12N 2501/2302; C12N 2501/2315; C12N 2501/2307; C12N 5/0636; G01N 33/5011; G01N 33/564; G01N 2800/52; G01N 33/505; G01N 33/566; Y10S 434/81; A61N 5/10; A61K 2300/00; A61K 45/06; A61K 2039/5158; A61K 35/17; A61K 39/0011; A61K 2039/57; A61K 38/2013; A61K 38/2086
See application file for complete search history.

(56) References Cited

U.S. PATENT DOCUMENTS

2010/0021472 A1 1/2010 Srikrishna
2010/0215622 A1 8/2010 Wang

FOREIGN PATENT DOCUMENTS

WO WO2007037780 * 4/2007

OTHER PUBLICATIONS

Le et al., Incubation of antigen-sensitized T lymphocytes activated with bryostatin 1 +ionomycin in IL-7 +IL-15 increases yield of cells capable of inducing regression of melanoma metastases compared to culture in IL-2, Cancer Immunol. Immunother. 58, 1565-1576, 2009.*
Cha et al., IL-7 +IL-15 are superior to IL-2 for the ex vivo expansion of 4T1 mammary carcinoma-specific T cells with greater efficacy against tumors in vivo. Breast Cancer Res. Treat. 122, 359-369, 2010.*
Lin S-J et al. Effect of interleukin-15 on effector and regulatory function of anti-CD3/anti-CD28—stimulated CD4+ T cells. Bone Marrow Transpl. 37, 881-887, 2006.*
Le et al., Gemcitabine directly inhibits myeloid derived suppressor cells in BALB/c mice bearing 4T1 mammary carcinoma and augments expansion of T cells from tumor-bearing mice. Int. Immunopharm., 9, 900-909, 2009.*
Morales et al., Adoptive transfer of HER2/neu-specific T cells expanded with alternating gamma chain cytokines mediate tumor regression when combined with the depletion of myeloid-derived suppressor cells. Cancer Immunol. Immunother., 58, 941-953, 2009.*
Gabrilovich; Nagaraj, "Myeloid-derived-suprresor cells as regulators of the immune system", Nat Rev Immunol, Mar. 2009, pp. 162-174, vol. 9, No. 3.
Dugast et al, "Myeloid-Derived Suppressor Cells Accumulate in Kidney Allograft Tolerance and Specifically Suppress Effector T Cell Expansion", The Journal of Immunology, 2008, pp. 7898-7906, vol. 180.
Ostrand-Rosenberg; Sinha, "Myeloid-Derived Suppressor Cells: Linking Inflammation and Cancer", The Journal of Immunology, 2009, pp. 4499-4506, vol. 182.

* cited by examiner

*Primary Examiner* — Elly-Gerald Stoica
(74) *Attorney, Agent, or Firm* — Whitham Curtis Christofferson & Cook, PC

(57) ABSTRACT

Methods for the ex vivo generation of cells of the innate (NKT cells and NK cells) and adaptive (T cells) immune systems for use in adoptive cell transfer (ACT) are provided. The NKT cells render T cells resistant to immune suppression (e.g. they are resistant to the effects of myeloid-derived suppressor cells (MDSCs)). The method involves culturing disease-primed immune cells (obtained from a cancer patient or from a patient with an infectious disease) with i) bryostatin and ionomycin (B/I) to activate and differentiate the cells; followed by sequentially culturing the cells with a) a combination of IL-7 and IL-15 and then b) IL-2, to further differentiate the cells and to render them immune resistant. The resistant immune cells are used to treat and prevent cancer and infectious diseases.

13 Claims, 9 Drawing Sheets

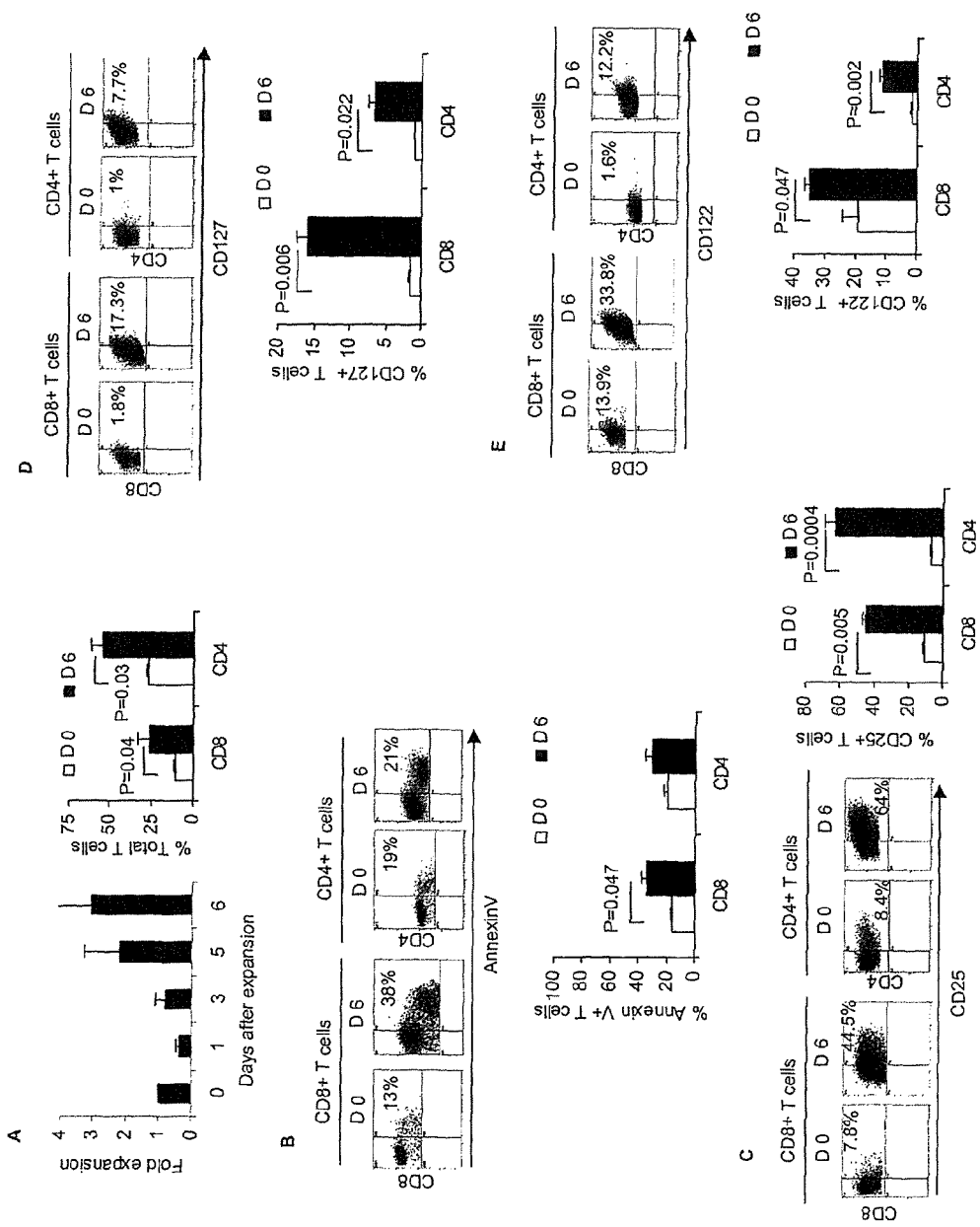
Figure 1A-E

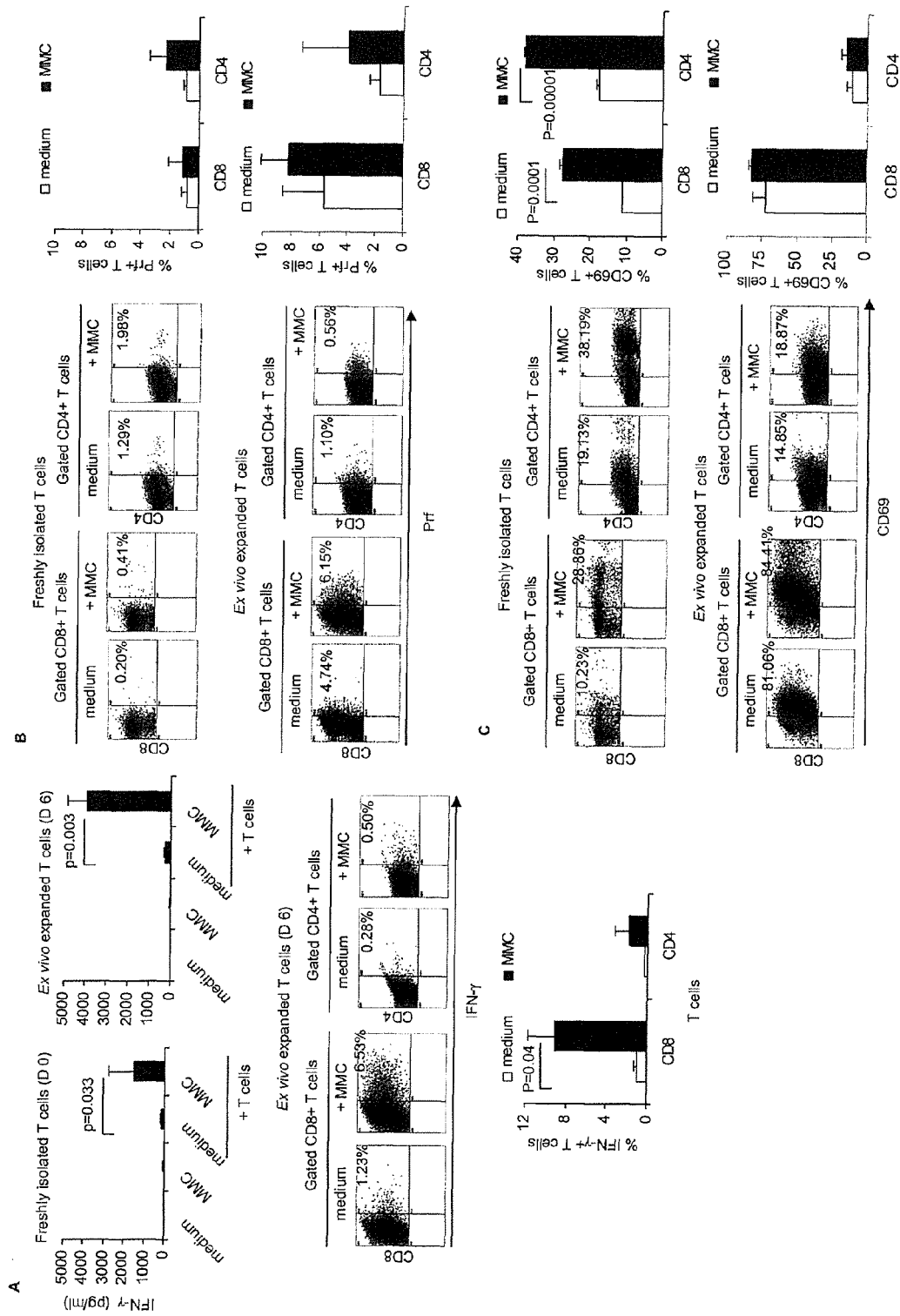
Figure 2 A-C

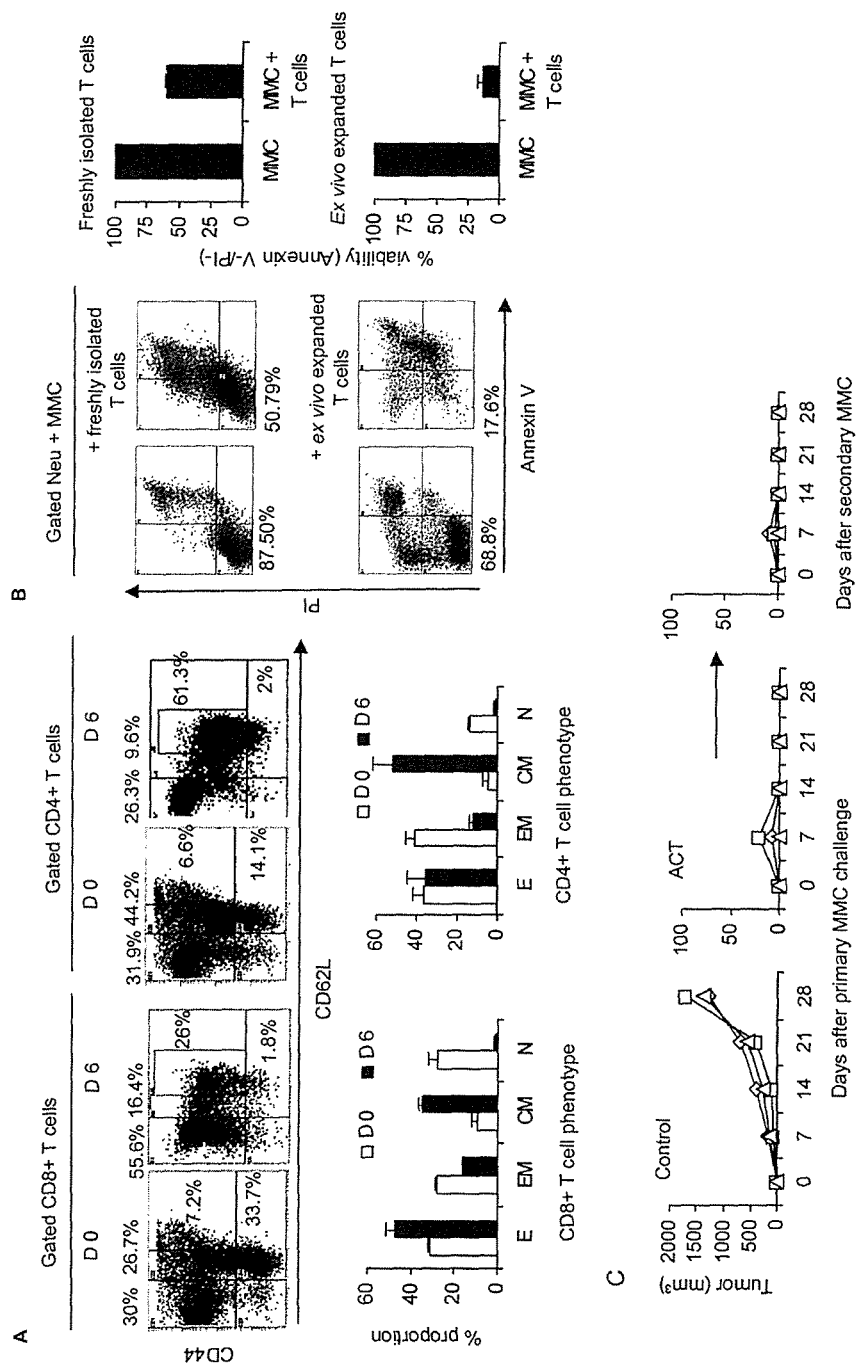
Figure 3A-C

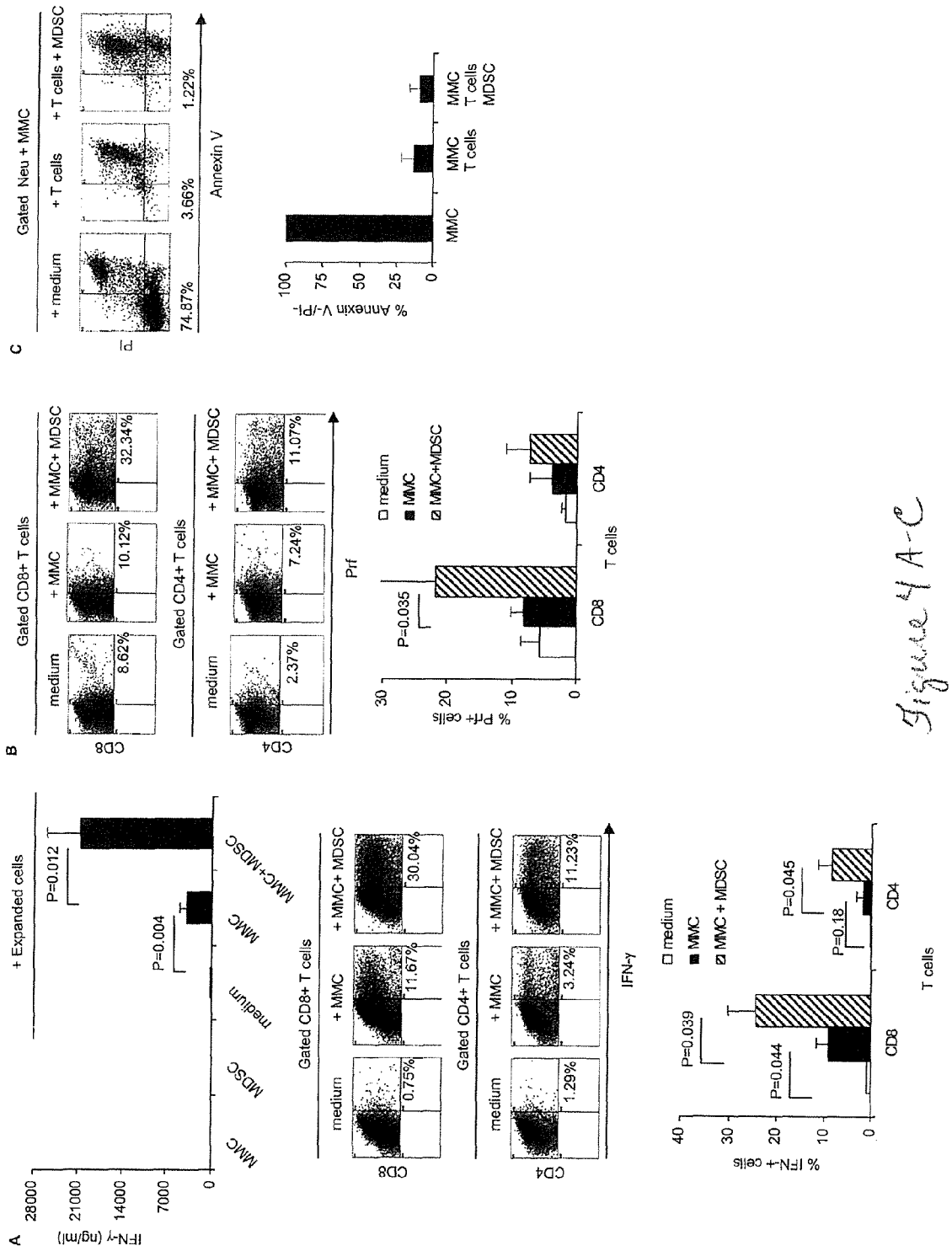
Figure 4 A-C

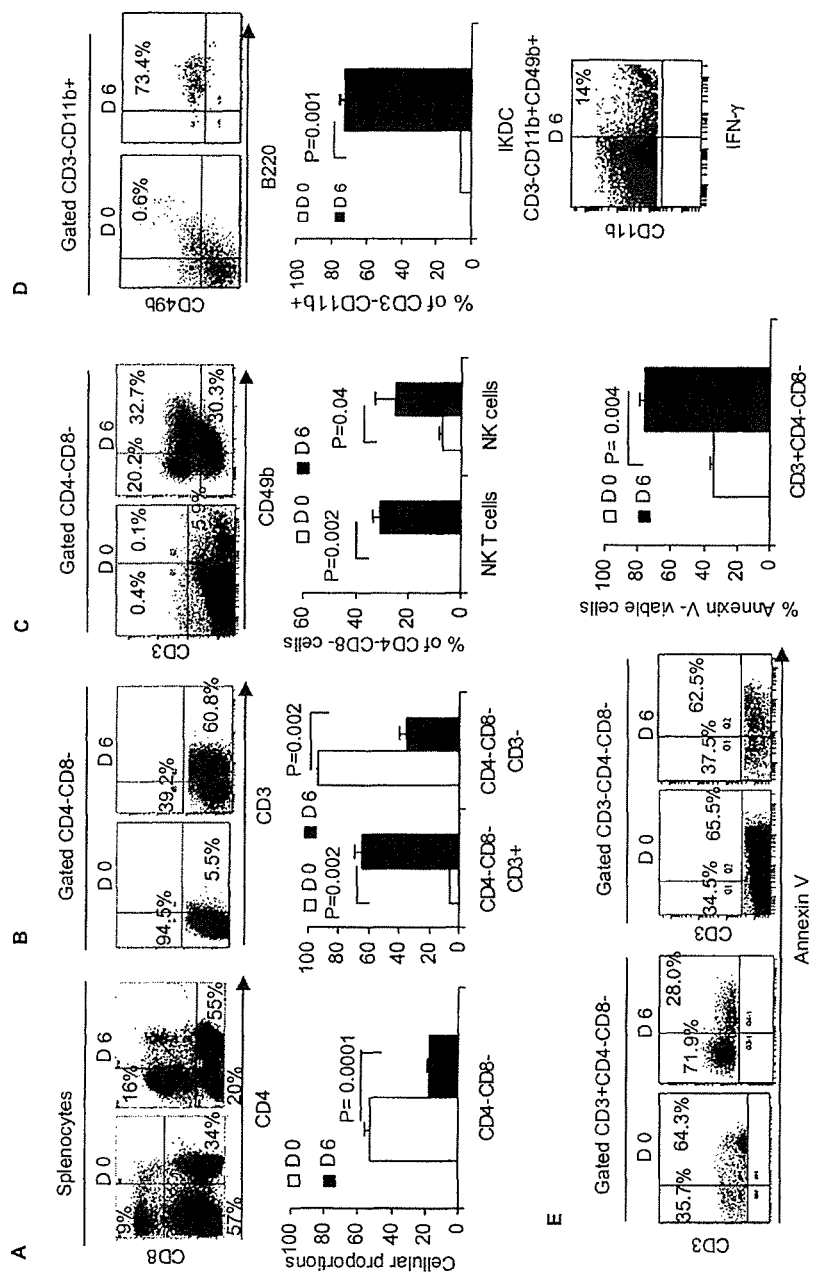
Figure 5A-E

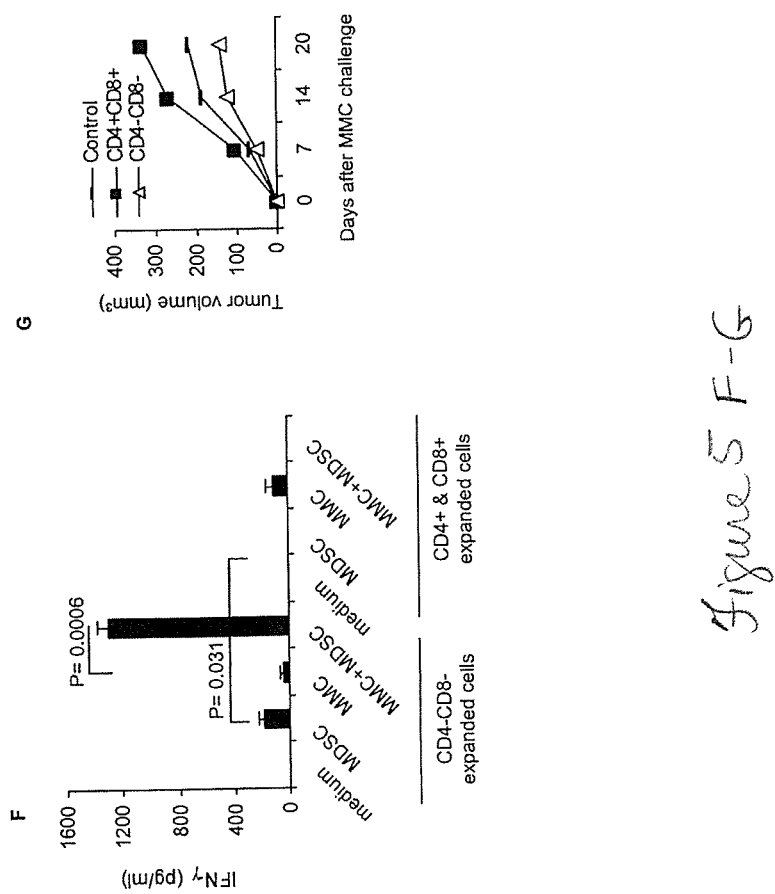
Figure 5 F-G

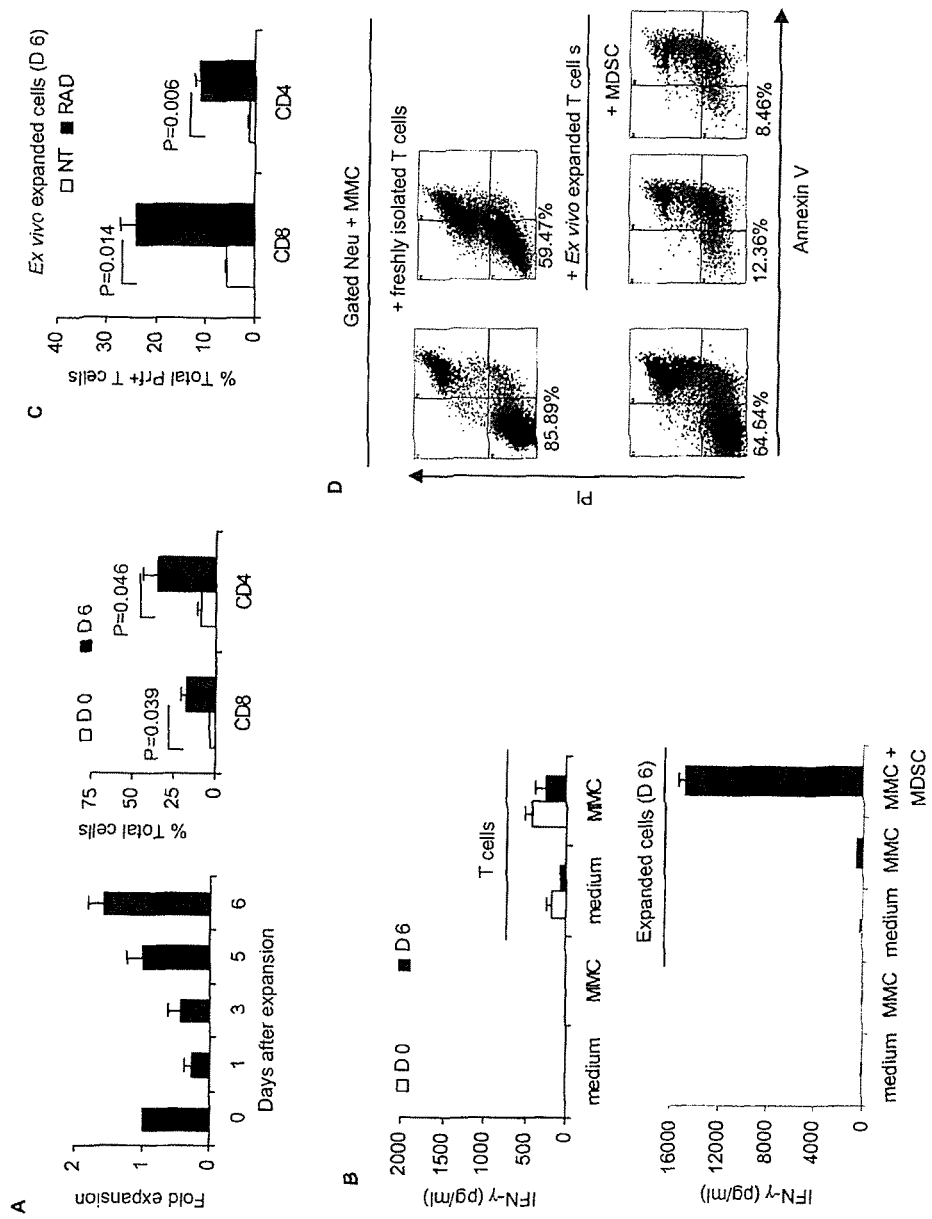

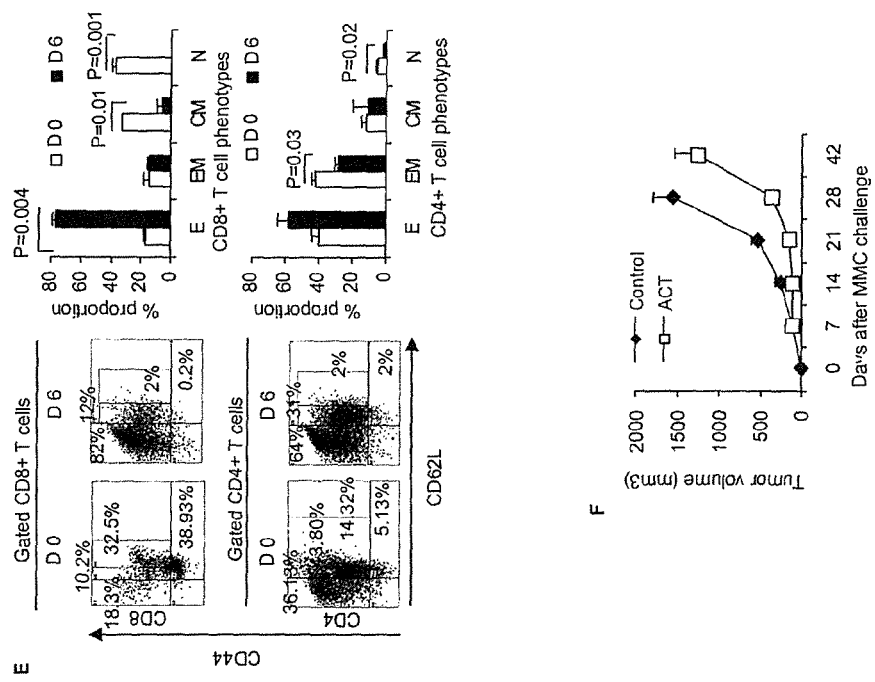
Figure 6 E-F

A.
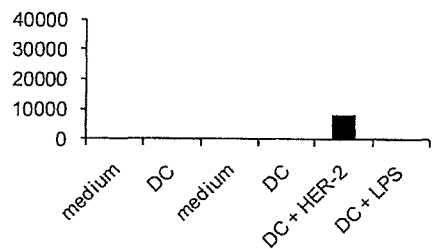
B.
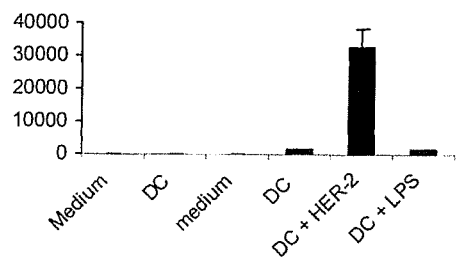
C.
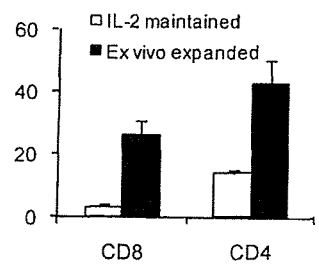
Figure 7A-C

US 8,741,642 B2

METHODS FOR PRODUCING AUTOLOGOUS IMMUNE CELLS RESISTANT TO MYELOID-DERIVED SUPPRESSOR CELLS EFFECTS

BACKGROUND OF THE INVENTION

1. Field of the Invention

The invention generally relates to the ex vivo generation of T cells for use in adoptive cell transfer (ACT). In particular, the invention relates to a step-wise combination protocol for generating T cells that are resistant to immune suppression, for use in the prevention and treatment of e.g. cancer and infectious disease.

2. Background of the Invention

When a cancerous tumor develops in a patient, the patient's immune system typically responds to the presence of the tumor by generating immune cells [e.g. immune effector cells such as lymphocytes, macrophages, dendritic cells, natural killer cells (NK cells), NKT cells, cytotoxic T lymphocytes (CTLs), etc.] that attack the tumor. However, depending on the characteristics of the tumor, the immune response, and other factors, the response may not be sufficient to completely destroy the cancer cells.

The technique of adoptive cell transfer (ACT, or, alternatively, adoptive immunotherapy, AIT) is used as a cancer treatment to augment an insufficient immune response. The rationale for the use of ACT in treating cancer is based on overcoming the low frequency of endogenous tumor-reactive T cells. For ACT, T cells that have a natural or genetically engineered reactivity to a patient's cancer are generated in vitro by ex vivo activation, expansion, and directed differentiation toward the most effective phenotype(s), and are then transferred back into the cancer patient. For example, autologous T cells that are found with the tumor of a patient, which are already naturally trained to attack the cancerous cells, may be manipulated in this manner. The expanded cytotoxic T cells are then transferred back into the patient where they recognize, attack and (theoretically) eliminate the tumor. Initial studies of adoptive cell transfer, however, revealed that persistence of the transferred cells in vivo was too short to be effective, and that lymphodepletion of the recipient (e.g. by total body radiation) prior to administration, is required to eliminate regulatory T cells (which diminish T cell activity) as well as normal endogenous lymphocytes that compete with the transferred cells for homeostatic cytokines which are necessary for full activity of T cells.

Several groups have shown that ACT directed against melanoma-associated antigens results in objective responses in animal models as well as in some melanoma patients (1, 2). To improve objective responses of ACT, a number of strategies have been developed which include using genetically modified lymphocytes (3), highly effective T cell phenotypes (4) and exposure of the T cells to common gamma-chain cytokines prior to administration (5). However, despite these modifications to ACT protocols, they are still not effective in all cases. One possible explanation is that, unlike animal models, cancer patients usually receive ACT after conventional therapies which could interfere with the efficacy of the donor T cells and be responsible for the variable results observed in patients. No comparative analysis has heretofore been performed to determine whether previous radiation therapy reduces or enhances the anti-tumor efficacy of ACT.

ACT has also been tested against breast cancer both in mouse models of breast cancer and breast cancer patients (6, 7). Unlike melanoma, ACT has never been shown to produce complete protection against breast tumors. Barriers to success include difficulty in the ex vivo expansion of tumor-reactive T cells (8), uncertainty as to the most relevant antigens, a lack of consensus as to the appropriate origin of the T cells to be used for expansion as well as phenotypic distribution of the most effective T cells, tumor stroma which act as a major barrier which prevents penetration of T cells into the solid tumor (10), and the presence of myeloid-derived suppressor cells (MDSC) in cancer patients during pre-malignant carcinogenesis which can abrogate anti-tumor efficacy of ACT (7, 9). Tumor-bearing animals and cancer patients have increased MDSCs due to the presence of the cancer, and MDSCs suppress anti-tumor T cells. As a result, in many cases, patients' own immune system fails to protect them against cancers. In addition, the presence of MDSCs usually results in the failure or attenuation of immunotherapy.

Some infectious disease agents also have the ability to evade immune clearance by suppressing the immune system. For example, infection with influenza A virus (IAV) results in the expansion of myeloid-derived suppressor cells (MDSC), which in turn suppresses IAV-specific immune responses (De Santo C, Salio M, Masri S H, Lee L Y, Dong T, Speak A O, Porubsky S, Booth S, Veerapen N, Besra G S, Gröne H J, Platt F M, Zambon M, Cerundolo V. Invariant NKT cells reduce the immunosuppressive activity of influenza A virus-induced myeloid-derived suppressor cells in mice and humans. J Clin Invest. 2008 December; 118(12):4036-48).

There is an ongoing need to investigate these factors and to modulate ACT protocols in order to achieve higher levels of success in tumor eradication for all types of cancer, and for the treatment of infectious diseases. In particular, there is a great need to develop an effective ACT protocol for the treatment of breast cancer.

SUMMARY OF THE INVENTION

An improved method for the ex vivo differentiation and expansion of disease-primed immune cells has been developed. The resulting immune cells are resistant to inactivation or suppression of the immune system, e.g. they are resistant (refractory) to the effects of immune suppressor cells such as myeloid-derived suppressor cells (MDSCs), and are thus suitable for use in ACT. The resistant cells are generated from disease-primed immune cells such as tumor-primed T cells or T cells that have been exposed to an infectious agent using a step-wise, combination ex vivo procedure. The procedure includes the steps of: 1) obtaining disease-primed immune cells (which may include tumor-primed T cells in a sample of peripheral blood mononuclear cells (PBMCs) from a tumor-bearing patient; or infectious-disease-primed immune cells from a patient with an infectious disease); 2) activating and differentiating the primed immune cells using bryostatin 1/ionomycin (B/I) in the presence of IL-2; followed by 3) expansion and further differentiation of the immune cells by sequential exposure of the cells to: first, a combination of IL-7 and IL-15 gamma-chain cytokines, and then, to the cytokine IL-2. Of note, the initial exposure to IL-2 may occur while the cells are still being cultured with IL-7 and IL-15, i.e. for a period of time, the cells are exposed to all three cytokines together. The cells are then washed to remove all such agents, and then cultured with IL-2 alone. The resulting immune cells are activated, differentiated and resistant to immune suppression. Therefore, when the resistant immune cells are administered to a patient e.g. as ACT cancer or infectious disease therapy, they are not susceptible to inactivation by the effects of the patient's innate or existing immune suppression mechanisms. As a result, the ACT therapy provides long-term protection against, e.g. cancer metastasis and recurrence. Or against infectious disease persistence or reemergence. In one embodiment, the disease that is treated using the protocols of the invention is an epithelial neoplasm such as breast cancer.

The proposed cytokine formulation described herein generates immune cells, including T cells, NKT cells and NK cells, that are refractory to immune suppressive function of MDSC and thus can actively fight the tumor. In addition, these immune cells can also reject the tumor without depleting regulatory T cells (Tregs). Therefore, adoptive cell therapy by means of this protocol can be applied to any type of carcinoma. The protocol can also be used in the prevention and/or treatment of infectious diseases where increased MDSC or other immune suppressive pathways prevent effective innate immunity and immunotherapy. In fact, cancers that fight the immune system by increasing MDSCs can be treated by this protocol.

The invention also clarifies patients' eligibility for the treatment by showing that tumor-bearing animals that had recently received local radiation therapy become ineligible for the treatment whereas tumor-bearing animals who received no prior treatment remain eligible. Thus, patients who have received conventional therapies, including radiation therapy, within about one month are not eligible for the present protocol. However, patients who have not received other therapies, or who have received e.g. radiation therapy but relapsed after a few (>1) months are eligible.

Patient accrual (the process of enrolling patients into a clinical trial) is a major challenge because patients frequently do not want to risk their lives by participating in a trial at the cost of not receiving conventional therapies. Patients usually participate in trials only after they have received conventional therapies and, unfortunately, such pre-treatments have already altered their immune systems. The present protocol, however, is advantageous in that it can be applied as neoadjuvant therapy before patients have received any other treatment, i.e. the present method is applied as treatment given to a patient to reduce tumor size before future operations or other procedures such as radiation therapy. As a result, patients do not have to forego conventional therapies thereafter. This approach improves patient accrual. In addition, in some cases, the therapeutic protocol described herein results in sufficient regression of metastatic cancer so that patients may not need to receive conventional therapies when their tumor relapses. This is a beneficial outcome, since conventional therapies may be extremely invasive and/or toxic, causing severe side effects. In contrast, the present protocol is advantageously non-invasive and lacks toxicity and side effects (such as an autoimmune reaction) because it uses autologous peripheral blood of the patient as a source of immune cells. PBMCs can be collected from the patients at the time of breast cancer diagnosis, expanded by the proposed protocol, and stored at −120 degree centigrade. Patients can then receive conventional therapies and when they end up with relapse of tumor that may be refractory to chemotherapy, their expanded immune cells can be used for the treatment of recurring cancer.

The method can also be practiced to treat individuals who suffer from infectious diseases that elude immune surveillance or clearance, especially those which depress the immune system as a mechanism for increasing survival and/or reproduction of the etiological agent.

BRIEF DESCRIPTION OF THE DRAWINGS

FIG. 1: ex vivo expansion of tumor-primed T cells with the sequential common gamma-chain cytokines A) ex vivo expansion of splenocytes harvested from MMC-primed (tumor volume=500-2000 mm$^3$) female FVBN202 mice before and after activation with B/I and expansion with sequential common gamma-chain cytokines as determined by trypan blue exclusion (left panel) or flow cytometry analysis of gated CD8+ or CD4+ T cells (right panel). B) Viability of freshly isolated (D 0) and ex vivo expanded (D 6) T cells was determined by flow cytometry analysis of gated CD8+ or CD4+ T cells. Expression of CD25 (C), CD127 (D) and CD122 (E) were determined on gated CD8+ or CD4+ T cells before and after a 6-day expansion. Data represent five independent experiments.

FIG. 2. ex vivo expanded, MMC-primed T cells respond to MMC cells in vitro A) Tumor reactivity of freshly isolated (D 0) and ex vivo expanded (D 6) T cells was determined by a 24-hs culture of T cells in the presence or absence of irradiated MMC cells followed by the detection of IFN-γ in the supernatant (upper panel). Medium alone and MMC alone were used as negative controls for IFN-γ production. The MMC-specific IFN-γ production in gated CD8+ and CD4+ T cells was determined by flow cytometry analysis (lower panel). The MMC-specific expression of Prf (B) and CD69 (C) were determined in gated T cells. Data represent five independent experiments.

FIG. 3. Phenotypic distribution of tumor-reactive T cells and their anti-tumor efficacy in vitro and in vivo A) Phenotypic distribution of freshly isolated (D 0) and ex vivo expanded (D 6) splenic T cells was determined by flow cytometry analysis of gated CD8+ or CD4+ T cells. Distribution of T cell phenotypes including CD44+CD62L− effector (E: TE), CD44+CD62Llow effector memory (EM: TEM), CD44+CD62Lhigh central memory (CM: TCM) and CD44−CD62L+ naive (N: TN) was determined. B) Gated neu positive MMC cells were analyzed for apoptosis (Annexin V+/PI+) in the absence or presence of freshly isolated or ex vivo expanded T cells. C) CYP-treated FVBN202 mice (n=3) were inoculated with MMC cells and received no further treatment (left panel) or received ACT (middle panel). Animals that had rejected MMC following ACT were given rest for 2 months and then were challenged with MMC cells on the contralateral side (right panel). Data represent five independent experiments.

FIG. 4. ex vivo expanded T cells are resistant to MDSC The ex vivo expanded T cells were cultured with irradiated MMC in the presence or absence of MDSC. MMC-specific IFN-γ was detected in the supernatant of a 24-hs culture (A; upper panel) and in gated CD8+ or CD4+ T cells (A; lower panels). B) MMC-specific Prf production in gated CD8+ or CD4+ T cells was also determined. C) The ex vivo expanded T cells were cultured with viable MMC cells in the presence or absence of MDSC for 48 hs. Viability (Annexin V−/PI−) of gated neu positive MMC cells was determined by flow cytometry analysis. Data represent 3 independent experiments.

FIG. 5. ex vivo expanded T cells include non-T cells (NK T cells, NK cells and IPKDC) that are responsible for rendering T cells resistant to MDSC. Freshly isolated (D 0) and ex vivo expanded (D 6) splenic cells were analyzed for the presence of CD4−CD8− non-T cells and CD4+ or CD8+ T cells (A). Expression of CD3 on non-T cells was determined (B). Non-T cells were also analyzed to determine the proportion of NK T cells and NK cells (C). Cells were gated on CD3−CD11b+ DC population and analyzed for the expression of CD49b and B220 as well as IFN-γ to identify IKDC population (D). Viability (Annexin V−/PI−) of CD3+ and CD3− non-T cells was determined (E). ex vivo expanded splenocytes from MMC-primed FVBN202 mice were sorted into non-T cells (CD4−CD8−) and T cells (CD4+ plus CD8+). The sorted cells were cultured with irradiated MMC in the presence or absence of MDSC for 24 hs and IFN-γ production was determined in the supernatants (F). The sorted cells were used for ACT (n=3) at doses proportional to the unsorted cells, and tumor growth was determined (G). Data represent three independent experiments.

FIG. 6. in vitro and in vivo efficacy of the ex vivo expanded and MMC-primed T cells harvested from FVBN202 mice after radiation therapy. A) ex vivo expansion of splenocytes harvested from MMC-primed female FVBN202 mice who received 3 cycles of local radiation therapy (5 Gy) in 3-day intervals, before and after activation with B/I and expansion with sequential common gamma-chain cytokines as determined by trypan blue exclusion (left panel) or flow cytometry analysis of gated CD8+ or CD4+ T cells (right panel). B) Tumor reactivity of freshly isolated (D 0) and ex vivo expanded (D 6) T cells was determined by a 24-hr culture of T cells in the presence or absence of irradiated MMC followed by the detection of IFN-γ in the supernatant. Medium alone and MMC alone were used as negative controls for IFN-γ production. C) The MMC-specific IFN-γ production in gated CD8+ and CD4+ T cells derived from donor mice with no radiation treatment (NT) and radiation treatment (RAD) was determined by flow cytometry analysis. D) Gated neu positive MMC cells were analyzed for apoptosis (Annexin V+/PI+) in the absence of presence of freshly isolated or ex vivo expanded T cells. E) Phenotypic distribution of freshly isolated (D 0) and ex vivo expanded (D 6) splenic T cells was determined by flow cytometry analysis of gated CD4+ or CD8+ T cells. Data represent 3 independent experiments. F) CYP-treated FVBN202 mice (n=3) were inoculated with MMC and received no further treatment (control) or received the expanded cells derived from donors after the local radiation therapy (ACT). Data represent three independent experiments.

FIG. 7. Patient with breast cancer harbors peripheral HER-2/neu-specific T cell precursors which can be activated by B/I activation and expanded with common gamma-chain cytokines A) T cells maintained with low dose IL-2 (40 U/ml) for 6-7 days were cultured in the presence or absence of autologous DC and presence or absence of recombinant human HER-2/neu for 24 hs. IFN-γ production was detected in the supernatant of triplicate wells. B) B/I activated and common gamma-chain cytokine expanded T cells were cultured in the presence or absence of autologous DC and presence or absence of recombinant human HER-2/neu for 24 hs. IFN-γ production was detected in the supernatant of triplicate wells. C) IL-2 maintained T cells (white bars) and ex vivo expanded T cells (black bars) were stained with anti-CD4, anti-CD8 and anti IFN-γ antibodies in order to determine cellular source of HER-2/neu-specific IFN-γ production. Data represent two independent experiments.

DETAILED DESCRIPTION

A number of key barriers to effective ACT therapy have been overcome in order to develop a novel cancer treatment that produces objective responses against primary tumors, including breast tumors, and to generate long-term memory against recall tumor challenge. The treatment method employs an optimized combination of steps of ex vivo treatment of immune cells which include tumor-primed T cells. Significantly, the immune cells are obtained from a cancer patient prior to receipt of any other type of therapy, e.g. prior to recent treatment of the tumor or tumors with radiation. According to the method, immune cells, which include tumor-primed (tumor sensitized, tumor-reactive) T cells, are harvested or obtained from a cancer patient with at least one tumor, e.g. an epithelial neoplasm such as a breast cancer tumor. The immune cells are then subjected to an antigen-free protocol for selective activation using bryostatin 1/ionomycin (B/I) and IL-2 as previously described (7, 11). Bryostatin 1 activates protein kinase C and ionomycin increases intracellular calcium (12, 13). Together, B/I mimic signaling through the CD3/TcR complex and lead to activation, differentiation and proliferation of the tumor-primed immune cell sample. Most recently, it was reported that bryostatin 1 can act as a TLR-4 ligand and also activate innate immunity (14). This property of bryostatin 1 may make it a useful drug for in vivo use in order to induce the innate immune responses in addition to T cell responses. According to the invention, the next step is expansion and further differentiation of the B/I activated immune cells by sequential exposure to common gamma-chain cytokines: first to IL-7 and IL-15 simultaneously, and then to relatively low concentrations of IL-2. In some embodiments, IL-2 is first added to the culture which already includes IL-7 and IL-15. The cells are then washed to remove all the cytokines, and IL-2 alone is added back to the cells for a further step of culturing. This ex vivo protocol thus induces differentiation and expansion of the immune cells, including the tumor-reactive T cells, in the sample. At the end of this combination protocol, the immune cells include central memory T cells (TCM) and effector T cells (TE) as well as cells of the innate immune system and non-T cells. As described in the Examples section below, the expanded cells are resistant to the effects of MDSCs and are capable of generating long-term memory responses against the tumor in a FVBN202 transgenic mouse model of HER-2/neu overexpressing breast carcinoma. HER-2/neu-specific T cells from peripheral blood mononuclear cells (PBMCs) of a breast cancer patient were also expanded using this method.

Subjects with infectious diseases, especially infectious diseases which depress the immune system, may also be treated with immune cells produced using the protocols described herein. This aspect of the invention is described in detail below.

The protocol includes collecting immune cells from tumor-bearing mammals such as humans, and processing them for from about 4 to 8 days, e.g. about 4, 5, 6, 7, or 8 days, and usually for about 6 days, before infusing the processed cells back into the patient. Cells that are used for the procedure may be, for example, peripheral blood mononuclear cells (PBMCs), or immune cells derived from tumor-draining nodes of patients that can be obtained by biopsy. Preferably, the cells are PBMCs. Those of skill in the art are familiar with procedures for harvesting cells and with accepted procedures for treatment of the cells in preparation for cell culture. Briefly, PBMCs are harvested from cancer patients (e.g. breast cancer patients) using 100-200 ml blood. After Ficoll density gradient separation, PBMCs are subjected to a multi-step processing in vitro.

The steps of the immune cell processing protocol include activation of the harvested, tumor-primed immune cells with bryostatin-1/ionomycin (B/I), in the presence of relatively high levels of IL-2. In other words, the newly harvested cells are cultured with (i.e. in the presence of) B/I. Those of skill in the art are familiar with such culture procedures and suitable culture conditions. For example, cells are typically cultured with a concentration and ratio of B/I of about 5 nM to about 1 μM, e.g. 5 nM/1 μM, and with about 80 U/ml of IL-2. Cells are typically cultured in media such as RPMI 1640 supplemented with 10% Fetal Bovine Serum (FBS), under sterile conditions at a temperature of about 37° C., and usually under 5% $CO_2$. The duration of exposure to B/I is generally from about 8 to about 20 hours, and usually from about 14 hours to about 18 hours, e.g. about 16 hours. B/I activation mimics intracellular signals that result in T cell activation by increasing protein kinase C activity and intracellular calcium, respectively. This protocol specifically activates tumor-specific T cells while killing irrelevant T cells.

Following incubation with B/I, the immune cells are washed and then cultured with a combination of the gamma-chain cytokines IL-7 and IL-15. Generally, the concentration of each of the cytokines in the medium ranges from about 1 to about 20 ng/ml, and is usually from about 5 to about 15, e.g. about 10 ng/ml of each cytokine. Culture temperature and other conditions remain as described above. The length of time of IL-7/IL-15 culture is generally from about 10 to about 40 hours, and may be from about 15 to about 30 hours, and is usually about 24 hours.

On e.g. the second day of culturing with IL-7/IL-15 (e.g. after the typical 24 hour incubation with IL-7/IL-15, the cells are pulsed with IL-2, i.e. IL-2 is added to the culture medium that already contains IL-7 and IL-15. The amount of IL-2 that is added is generally in the range of from about 10 to about 30 units/ml, and is generally about 20 u/ml. The cells are cultured as described above with these 3 cytokines for from about 10 to about 40 hours, and or from about 15 to about 30 hours, and usually for about 24 hours.

On the day following the end of the culture with three cytokines, the cells are washed to remove cytokines, split into a plurality of culture containers, and then further cultured in the presented of IL-2 alone. For this incubation, the amount of IL-2 that is used is generally greater than that which is used for the 3 cytokine incubation, and ranges from about 20 to about 60 u/ml, or from about 30 to about 50 u/ml, and is usually about 40 u/ml. The cells are cultured in the presence of IL-2 as the sole cytokine for at least one, and preferably for at least 2 days or more.

The procedure results in production of immune cells which are resistant to the effects of MDSCs and are capable of generating long-term memory responses against the tumors that were present in the patient at the time the original immune cell sample was obtained.

A brief summary of the protocol is as follows: 1) collection of immune cells from tumor-bearing subject; 2) activation of immune cells with B/I for about 16 hours; 3) immune cells are cultured in the presence of IL-7 and IL-15 (10 ng/ml) for 24 hours; 4) on day 3, cells are pulsed with IL-2 (20 U/ml); 5) on day 4, cells will be washed, split, and cultured with IL-2 (40 U/ml) for an additional 2-3 days.

The total time required to obtain MDSC resistant cells from tumor-activated immune cells is generally from about 5 to about 8 days, e.g. about 4, 5, 6, 7, or 8 days, and usually about 6 days. In some embodiments, this period of time includes harvesting or obtaining the immune cells from a patient, in which case processing is typically started on the same day. However, in some embodiments, tumor-primed immune cells are obtained from a patient and then preserved (e.g. by freezing) and processed thereafter. This is especially useful when a patient is in imminent need of receipt of conventional cancer therapies such as chemotherapy or radiation, which might have a deleterious effect on the immune system of the patient, e.g. a negative effect on the patients immune cells which prevents them from being amenable to successful processing as described herein. Harvested immune cells may be stored, e.g. at low or ultralow temperatures such as from −40 to −150° C. Storage is from a period of time ranging e.g. up to several years at −120° C.

After MDSC resistant immune cells are produced, they are administered to a patient in need thereof, usually the patient from which the original immune cell sample was obtained. Those of skill in the art are familiar with techniques for administering cells to a patient. Generally, the cells are harvested from culture, washed, and re-suspended in a physiologically (biologically) compatible carrier. Issued U.S. Pat. No. 8,034,334 and published US patent applications 20110236363 and 20110250233, the complete contents of both of which are hereby incorporated by reference) provide general guidance in this respect.

The immune cells may be administered by any suitable route known in the art, generally via intra-arterial or intravenous infusion, which usually lasts approximately 30-60 min. Other examples of routes of administration include intraperitoneal, intrathecal, intratumor and intralymphatic. The cells may be administered as a single bolus, or multiple administrations may be used.

Exemplary pharmaceutically acceptable carriers include but are not limited to various suitable liquid vehicles such as distilled water, physiological saline, phosphate-buffered saline (PBS), aqueous solutions of dextrose, various lipophilic solvents or vehicles such as fatty oils (for example, sesame oil, or synthetic fatty acid esters such as ethyl oleate or triglycerides), etc. In some embodiments, the pharmaceutically acceptable carrier is pharmaceutically acceptable for use in a human. A composition which includes the cells and the carrier may optionally also include auxiliary additives such as, for example, anti-oxidants, bacteriostats, bactericidal antibiotics, suspending agents, buffering agents, substances which increase or maintain the viscosity of the suspension, stabilizers, various immune adjuvants known in the art (e.g. Freund's complete adjuvant, inorganic salts such as zinc chloride, calcium phosphate, aluminum hydroxide, aluminum phosphate, saponins, polymers, lipids or lipid-fractions such as Lipid A, monophosphoryl lipid A, modified oligonucleotides, etc.), and the like. The formulations can be presented in unit-dose or multi-dose containers, for example sealed ampoules and vials, and can be stored in a frozen or freeze-dried (lyophilized) condition and reconstituted immediately prior to use.

Any suitable dose of immune cells can be administered. Preferably, from about $1 \times 10^{10}$ to about $10 \times 10^{10}$ cells are administered, e.g. about 1, 2, 3, 4, 5, 6, 7, 8, 9, or $10 \times 10^{10}$ cells are administered.

The treatment methods described herein may be repeated is necessary or considered prudent by medical professionals (usually a physician) who is experienced in treating cancer. For example, the patient may undergo the entire procedure, from donation of cells to receipt of resistant cells, only once, or repeatedly, e.g. every month, or every 2, 3, 4, 5, or 6 month, or yearly, or every 2 years, etc., as needed to keep the cancer in check. Alternatively, cells may be harvested from the donor and frozen until processed as described herein, and used then used at these time intervals. Alternatively, processed, resistant cells can also be preserved (e.g. frozen as described above) for use when needed.

As discussed herein, the immune cells produced by the methods of the invention are generally used to treat cancer patients via ACT. The cells may be administered prophylactically (e.g. to a patient that has previously had cancer and may be or is susceptible to relapse in order to prevent recurrence, or a person who is at high risk of developing cancer, or who is suspected of having developed cancer but does not yet have a definitive diagnosis); or the cells may be administered to treat a known cancer. The cancer may be primary or metastatic. Types of cancer that may be prevented or treated include but are not limited to various epithelial neoplasms such as breast cancer, prostate cancer, ovarian cancer, cervical cancer, melanoma, colon cancer, lung cancer and stomach cancer.

Administration of the MDSC resistant immune cells of the invention typically results in tumor regression in about 3-4 weeks. An advantage of the method is that long-term protection thereafter is also provided, since the T-cells (and other cells in the composition) retain a "memory" of the cancer antigens present on the tumor cells that were present in the patient from whom the initial sample of tumor primer immune cells were obtained. While complete remission may occur, those of skill in the art will recognize that much benefit can accrue from partial regression of the tumor as well, since this may provide a window of opportunity to utilize other cancer therapies to advantage. Further, simply lengthening the life of or improving the quality of life of a cancer patient is of value, even if a permanent cure is not affected.

The methods of the invention may be utilized in combination with other cancer treatment therapies including but not limited to: surgery, chemotherapy, radiation therapy, administration of cytokines such as gamma chain cytokines, hormone therapy, antibody therapy. Generally, the ACT protocol described herein is carried out prior to other therapies and, if successful, may preclude the need for other therapies. The ACT may also be carried out after conventional therapies in order to prevent tumor relapse. However, lymphocytes must be obtained from patients prior to other therapies, expanded and stored at −120 until use. The present methods may be carried out at any time and with any combination of other cancer therapies, with the caveat that immune cells from a patient who has received radiation therapy within about the previous month are not optimal for the procedure, unless his/her immune cells were obtained prior to the radiation treatment, as described previously. A patient who has had radiation therapy should not be an immune cell donor as described herein until after at least about 1, 2, 3, 4 or more weeks, after receipt of radiation, and usually after at least about one month, although in some cases the mere chance of success may be worth trying the procedure earlier.

Usually, but not always, the patient who receives the cells (the recipient) is also the patient from whom the cells are harvested or obtained, i.e. the donor. In other words, usually the cells that are provided to a cancer patient are autologous, low affinity T cells (patients' own T cells without genetic manipulation) rather than high affinity T cells (T cells with TcR transgene for the tumor antigen) in order to reduce risk of tumor escape and recurrence following initial tumor rejection. However, in some embodiments, generically engineered cells (which may be the patient's own cells that have been genetically manipulated) are used. In addition, in some embodiments, the cells may be provided to or received from another patient, i.e. the cells are allogenic cells. Usually, the patients or subjects who donate and receive the immune cells are mammals, generally humans. However, this need not always be the case, as veterinary applications are also contemplated.

In some embodiments, the patient that is treated using the protocol described herein is an infectious disease patient. PBMC can be collected and expanded from patients with chronic infectious diseases such as tuberculosis and infused back into the patients to clear the infection. In this case, the immune cells that are taken from the patient are "infectious disease primed" cells.

Exemplary infectious disease that may be prevented or treated, or recurrences of which may be prevented or treated, include but are not limited to: tuberculosis, human papillomavirus (HPV), and other viral infections.

Various embodiments of the invention are described in the following Examples, which should not be considered as limiting the invention in any way.

EXAMPLES

Example 1

Attempts to cure breast cancer by means of adoptive cellular therapy (ACT) have not been successful. This is primarily due to the presence of tumor-induced immune suppressive mechanisms as well as the failure of tumor-reactive T cells to provide long-term memory responses in vivo. In order to address these clinically important challenges an ex vivo protocol has been developed for the expansion of tumor-reactive immune cells obtained from tumor-bearing animals prior to or after local radiation therapy. An antigen-free protocol which included bryostatin 1/ionomycin (B/I) and sequential common gamma-chain cytokines (IL-7/IL-15+IL-2) was employed. The protocol expanded tumor-reactive T cells as well as activated non-T cells, including NKT cells, NK cells and IFN-γ producing killer dendritic cells (IKDC) (Among these cells, T cells and NKT cells are important components of an effective ACT). Anti-tumor efficacy of T cells depended on the presence of non-T cells. The effector non-T cells also rendered T cells resistant to myeloid-derived suppressor cells (MDSC). Radiation therapy altered the phenotypic distribution and differentiation of T cells, and diminished the ability to generate central memory T cells (TCM). ACT by means of the expanded cells protected animals from tumor challenge and generated long-term memory responses against the tumor, provided that leukocytes were derived from tumor-bearing animals prior to radiation therapy. The ex vivo protocol was also able to expand HER-2/neu-specific T cells derived from the PBMC of a single patient with breast carcinoma.

This Example describes materials and methods used in the Examples that follow and also in the generation of data for FIGS. 1-7; additional detail regarding experimental procedures and results can be found above under "Brief Description of the Drawings".

Materials and Methods

Mouse Model

FVBN202 transgenic female mice (Charles River Laboratories) were used between 8-12 weeks of age throughout these experiments. These mice overexpress an unactivated rat neu transgene under the regulation of the MMTV promoter (15). These mice develop premalignant mammary hyperplasia similar to ductal carcinoma in situ (DCIS) prior to the development of spontaneous carcinoma (16). Pre-malignant events in FVBN202 mice include increased endogenous MDSC (16). These studies have been reviewed and approved by the Institutional Animal Care and Use committee (IACUC) at Virginia Commonwealth University.

Tumor Cell Lines

The neu overexpressing mouse mammary carcinoma (MMC) cell line was established from a spontaneous mammary tumor harvested from FVBN202 mice as previously described by our group (17). Tumor cells were maintained in RPMI 1640 supplemented with 10% fetal bovine serum (FBS). Mice were challenged with 3-4×10$^6$ MMC cells subcutaneously (s.c.) in the lower part of the mammary region close to the groin area.

Flow Cytometry

Flow cytometry analyses were performed as previously described previously (16, 18). Briefly, spleens were disrupted into a single cell suspension and 10$^6$ cells were aliquoted into each sample tube. Non-specific binding of antibodies to Fc receptors was blocked by incubating the cells with anti-CD16/32 antibody (Biolegend). Cells were stained with surface antibodies towards various markers and incubated on ice in the dark for 20 minutes, then washed twice with cell staining buffer (PBS, 1% FBS, 0.1% Sodium Azide) and fixed with 1% paraformaldehyde. For intracellular staining of perforin (Prf) and FoxP3, we followed the FoxP3 staining protocol provided by the manufacturer (Biolegend). Cells stained for granzyme B (GrB) and IFN-γ were fixed with 2.5% paraformaldehyde for 10 minutes on ice, washed twice with 0.1% saponin cell staining buffer, and then stained with the indicated antibodies. Cells were then washed twice with normal cell staining buffer and fixed with 1% paraformaldehyde. For Annexin V staining, cells were stained for respective surface markers, washed with cell staining buffer, and then washed with 1× Annexin V buffer (BD Pharmingen). The Annexin V staining protocol given in the product data sheet was then followed. Antibodies used for flow cytometry were purchased from Biolegend (FITC-, PE-, PE/Cy5-CD3, FITC-, PE-, PE/Cy5-CD4, FITC-, PE-, PE/Cy5-, APC-CD8, FITC-, PE/Cy5-CD11b, PE-, PE/Cy5-Gr1, FITC-, PE-CD25, FITC-CD44, PE-CD62L, PE-, APC-CD49b, PE-CD69, FITC-, PE-CD122, FITC-, PE-CD127, FITC-, PE-B220, PE-IFN-γ, PE-Foxp3) or eBiosciences (FITC-, APC-, PE-Prf, PE-, PE/Cy5-GrB). All antibodies were used at the manufacture's recommended concentrations. Multicolor data acquisition was performed on a BD FACSCanto II and analyzed using BD FACSDiva software.

Cell Sorting

In order to sort distinct cellular populations of splenocytes, $10^7$ cells were added to sample tubes in which Fc receptors were blocked and surface markers were stained with FITC-conjugated CD4 and PE-conjugated CD8 antibodies. Cells were then washed with sterile PBS supplemented with 2% FBS. T cells and non-T cells were sorted into 100% FBS using a BD FACSAria III cell sorter. Purity of sorted cells was greater than 98%.

Cytotoxicity Assay

Freshly isolated tumor-primed splenocytes or the ex vivo expanded cells were cultured with MMC at a 10:1 E:T ratio in 3 ml complete medium (RPMI-1640 supplemented with 100 U/ml of penicillin, 100 μg/ml streptomycin, 10% FBS, 10 mM L-glutamine and $5\times10^{-5}$ M 2-mercaptoethanol) with 20 U/ml of IL-2 (Peprotech) in 6 well culture dishes. After 48 hs cells were harvested and stained for neu (anti-c-Erb2/c-Neu, Calbiochem), Annexin V and PI according to the manufacturer's protocol (BD Pharmingen). Flow cytometry was used to analyze the viability of neu positive cells.

IFN-γ ELISA

Freshly isolated tumor-primed splenocytes or the ex vivo expanded cells were cultured in complete medium at a 10:1 ratio with irradiated MMC cells (14,000 rad) for 24 hs. Supernatants were then collected and stored at −80° C. until assayed. IFN-γ was detected using a Mouse IFN-γ ELISA set (BD Pharmingen) according to the manufacture's protocol.

Expansion of Effector T Cells from FVBN202 Mice

FVBN202 transgenic mice were inoculated with $4\times10^6$ MMC cells and splenocytes were harvested after 21-25 days. Splenocytes ($10^6$ cells/ml) were then stimulated in complete medium containing 15% FBS as well as Bryostatin 1 (5 nM)/Ionomycin (1 μM), and 80 U/ml of IL-2 for 16 hs, as previously described (12). Cells were then washed three times and cultured at $10^6$ cells/ml in complete medium with 10-20 ng/ml each of IL-7 and IL-15 (Peprotech). After 24 hs, 20 U/ml of IL-2 was added to the culture. On the next day cells were washed three times and cultured at $10^6$ cells/ml in complete medium with 40 U/ml of IL-2. Cells were split and cultured at $10^6$ cells/ml in complete medium with 40 U/ml of IL-2 every other day for a total of 6 days. After day 6, cells were then used for ACT or in vitro studies.

Adoptive Cellular Therapy (ACT)

Twenty four hours prior to ACT, FVBN202 mice were injected i.p. with CYP (100 mg/Kg) in order to induce lymphopenia. Mice were challenged with $3\times10^6$ MMC cells and then received $70\times10^6$ of the expanded cells by tail vein injection later the same day. Tumor growth was monitored by digital caliper and tumor volumes were calculated by: Volume $(v)=[L\ (length)\times W\ (width)^2]/2$.

Isolation of MDSC In Vitro

The Gr1+MDSC population was isolated using an EasySep-FITC selection kit from StemCell Technologies, as previously described (7, 19). Endogenous MDSC isolated from bone marrow or secondary lymphoid tissues have been shown to inhibit T cell responsiveness to anti-CD3/anti-CD28 antibodies (7, 19-22). Also, the Ly6C+Ly6G− subset but not the Ly6G+Ly6C+ subset isolated from FVBN202 mice was found to be suppressive (19). Because of the higher proportion of Ly6C+Ly6G− subset in tumor-bearing mice compared to tumor-free mice, the suppressive effects of MDSC isolated from tumor-bearing mice was greater using an optimal 2:1 ratio of T cells to MDSC (19). Therefore, in this study an optimal 2:1 ratio of splenic MDSC isolated from tumor-bearing FVBN202 mice was used.

Expansion of HER-2/neu-Specific T Cells from PBMC

Peripheral blood mononuclear cells (PBMC) were harvested from a breast cancer patient under Institutional Review Board (IRB) protocol HM10920. PBMC were cultured at 37° C. for 2 hs; adherent cells were used for the generation of monocyte-derived DCs in the presence of GM-CSF and IL-4, as previously described (17). Floater cells were split into two groups. One group was maintained with IL-2 (40 U/ml/$10^6$ cells) for 6-7 days until autologous DCs became available. Another group was activated with B/I and expanded with common gamma-chain cytokines. The expanded cells or IL-2 maintained cells were cultured with autologous DCs (4:1) in the presence or absence of recombinant HER-2/neu (100 ug/ml) or LPS (10 ug/ml). After 24 hs, supernatants and cells were collected and subjected to IFN-γ ELISA and flow cytometry analysis, respectively.

Recombinant HER-2/neu Protein

Extracellular domain (ECD) and intracellular domain (ICD) of human HER-2/neu protein were expressed in *E. coli* and purified by Ni-NTA-Agarose (Qiagen, Valentica, Calif.), as previously described (23). Concentration of the recombinant proteins was determined using the Bradford assay.

Statistical Analysis

Graphical data are presented as means with standard errors. Statistical comparisons between groups were made using Student's t test with P<0.05 being statistically significant.

Results

Sequential Common Gamma-Chain Cytokines Expand B/I-Activated T Cells Derived from Tumor-Bearing FVBN202 Mice It has previously been shown that activation of splenocytes (7) or tumor-draining lymphocytes with B/I could mimic T cell receptor signaling and selectively activate tumor-primed T cells (7, 20-22). Expansion of the B/I-activated T cells would then result in differential phenotype distribution depending on the cytokine formulation used during the expansion (7). Different combinations of IL-2, IL-7, IL-15 have previously been tested (7, 21, 22) and the superiority of an alternating sequence of common gamma-chain cytokines (IL-7+IL-15=>IL-2=>IL-7+IL-15) had been shown. However, anti-tumor efficacy of cells grown in alternating cytokines was limited in the neu transgenic tumor model because of a high level of endogenous MDSC in the FVBN202 transgenic mice, which was further increased during tumor challenge (7, 16). Therefore, we sought to determine whether a sequential common gamma-chain cytokine regimen (IL-7+IL-15 followed by IL-2) would improve anti-tumor efficacy of the expanded cells in FVBN202 mice. We first examined the composition of cells that were expanded with the sequential common gamma-chain cytokine formulation, and showed a three-four fold expansion of CD8+ and CD4+ T cells during a 6-day culture ex vivo (FIG. 1A). Although expanded CD8+ T cells showed reduced viability during the ex vivo culture (Annexin V+ CD8+ T cells: 13% to 38%, p=0.047; FIG. 1B), the proportion of CD25+, CD127+ and CD122+ T cells was significantly increased (6-8 fold increases of CD25+ cells, FIG. 1C; 7-9 fold increases of CD127+ cells, FIG. 1D; and 2-6 fold increases of CD122+ cells, FIG. 1E). There were marginal increases in the number of CD4+CD25+Foxp3+ T cells, accounting for only 2% of the gated CD4+ T cells after a 6-day expansion (not shown).

T Cells Expanded with Sequential Common Gamma-Chain Cytokines are Highly Responsive to neu+ MMC Cells In order to determine whether the ex vivo expansion of T cells enriched tumor-reactive T cells, production of IFN-γ, Prf, GrB as well as the expression of the CD69 early activation marker was determined in the presence or absence of irradiated neu+ MMC in vitro. Compared to freshly isolated splenocytes, the ex vivo expanded T cells showed greater IFN-γ production upon stimulation with MMC (average 1500 pg/ml vs. 4000 pg/ml, p=0.042; FIG. 2A, upper panel). T cells isolated from naive FVBN202 mice did not show IFN-γ production upon MMC stimulation in vitro (data not shown). Flow cytometry analysis of the ex vivo expanded cells determined that CD8+ T cells were the source of tumor-specific IFN-γ production (FIG. 2A, lower panel). Although no significant increases of Prf+ T cells was detected upon MMC stimulation, the proportion of Prf+CD8+ T cells was greater among the ex vivo expanded cells than freshly isolated splenocytes (average 1% vs. 7%, p=0.028; FIG. 2B). The presence of tumor-reactive T cells among freshly isolated splenocytes was further confirmed by detecting an increased proportion of CD69+ T cells upon MMC stimulation (FIG. 2C). The ex vivo expansion of CD8+ T cells resulted in an increased proportion of CD69+ early effector cells prior to MMC stimulation (average 10% vs. 81%, p=0.011; FIG. 2C) and after MMC stimulation (average 28% vs. 84%, p=0.001; FIG. 2C). Almost all T cells expressed GrB prior to and after a 6-day expansion ex vivo (not shown).

Ex Vivo Expanded T Cells are Enriched for CD44+CD62L− Effector (TE) and CD44+CD62Lhigh Central Memory (TCM) Phenotypes and Provide Complete Protection Against Primary as well as Recall Tumors CD44+CD62L− effector T cells (TE) and CD44+CD62Llow effector memory T cells (TEM) provide immediate protection against tumors whereas CD44+CD62Lhigh central memory T cells (TCM) are important for generating long-term protection. TCM are particularly important during recall tumor challenge. Ideally, the presence of both phenotypes can provide protection against primary and recall tumor challenges. Therefore, we sought to determine the phenotypic distribution of CD8+ and CD4+ T cells prior to and following the 6-day ex vivo expansion with sequential common gamma chain cytokines. Freshly isolated CD8+ T cells contained roughly equal proportions of TE (30%), TEM (26%) and CD44−CD62L+ naive T cells (TN: 33%). ex vivo expanded CD8+ T cells were enriched for TE (D 6: 55.6% vs. D 0: 30%, p=0.02) and TCM (D 6: 26% vs. D 0: 7.2%, p=0.008) (FIG. 3A). ex vivo expanded CD4+ T cells showed an unchanged proportion of TE (D 6: 31.9% vs. D 0: 26.3%) but were enriched for TCM (D 6: 61.3% vs. D 0: 6.6%, p=0.002). TN phenotypes almost disappeared in the expanded CD8+ T cells (D 6: 1.8% vs. D 0: 33.7%, p=0.009) and CD4+ T cells (D 6: 2% vs. D 0: 14.1%, p=0.003). Such a phenotypic distribution towards CD8+ TE and TCM suggests the potential for immediate as well as long-term memory responses against the tumor. We then performed in vitro cytotoxicity assays and in vivo tests of tumor growth inhibition in order to determine the anti-tumor efficacy of the expanded cells. Freshly isolated splenocytes or expanded T cells were cultured with viable neu+ MMC tumor cells in an effector:target (E:T) ratio of 10:1 for 2 days. Gated neu+ MMC cells were then analyzed for the detection of apoptosis as determined by Annexin V+/PI+ cells. As shown in FIG. 3B, freshly isolated T cells reduced viability of neu+ MMC from 87.5% to 50.79% (1.7 fold) while the ex vivo expanded T cells displayed greater cytotoxic function, reducing the viability of MMC from 68.8% to 17.6% (3.9 fold).

To test in vivo efficacy of expanded T cells, we used FVBN202 mice, which harbor increased MDSC because of premalignant mammary hyperplasia preceding spontaneous mammary tumors. Endogenous MDSCs were further increased upon MMC tumor challenge (7, 16). Here, we injected FVBN202 mice with cyclophosphamide (CYP) one day prior to ACT in order to generate a semi-lymphopenic condition. Animals were then challenged with MMC followed by i.v. injection of the ex vivo expanded cells 6-8 hs after the MMC challenge. Recipients of ACT rejected the neu+ MMC (FIG. 3C), despite the presence of MDSC before and 7 days after MMC challenge (not shown). All control mice that had received CYP alone developed tumors. In order to determine memory responses, ACT-treated mice were challenged on the contralateral side with MMC two months after the rejection of primary MMC cells. During recall tumor challenge, animals received neither CYP nor ACT, yet all the mice rejected the recall tumors (FIG. 3C). In order to determine which T cell phenotypes were effective in vivo, we sorted T cells into CD62L−/low (TE/TEM) and CD62Lhigh (TCM), and performed ACT with the sorted cells. No protection was observed against the tumors (data not shown). These data suggests critical interactions among tumor-reactive T cell phenotypes which requires further investigation.

The Ex Vivo Expanded T Cells Acquire Resistance to Inhibitory Function of MDSC

Since the ex vivo expanded cells protected FVBN202 mice against primary and recall tumor challenges even in the absence of MDSC depletion (FIG. 3C), we sought to determine whether the ex vivo expanded cells were resistant to MDSC in vitro. We have previously reported that MDSC isolated from bone marrow or spleens of tumor-bearing FVBN202 mice can inhibit T cell responsiveness to CD3/CD28 stimulation (7, 19). MDSC can also inhibit MMC tumor-specific IFN-γ production by T cells expanded with alternating common gamma-chain cytokines (not shown). Therefore, splenocytes expanded with sequential common gamma-chain cytokines were cultured for 24 hr in the presence or absence of irradiated MMC (10:1 ratio of expanded cells to MMC) to show their reactivity with MMC in the presence or absence of splenic MDSC (2:1 ratio of expanded cells to MDSC). Supernatants were collected and subjected to IFN-γ ELISA. T cells were also analyzed for the expression of IFN-γ, Prf, GrB, and CD69. As shown in FIG. 4A (upper panel), the ex vivo expanded cells produced IFN-γ in the presence of MMC (p=0.004) as expected. Importantly, addition of MDSC not only failed to suppress MMC-specific IFN-γ secretion by the expanded cells, but also increased the IFN-γ response (p=0.012). Flow cytometry analysis of the expanded cells determined that CD8+ T cells were the main source of MMC-specific IFN-γ production (FIG. 4A, lower panel). Addition of MDSC increased MMC-induced production of IFN-γ by both CD8+ and CD4+ T cells. Increasing the dose of MDSC did not increase MMC-specific production of IFN-γ by the expanded T cells (data not shown). The presence of MDSC also resulted in an increased production Prf in CD8+ T cells upon MMC stimulation (p=0.035, FIG. 4B). There was no IFN-γ or Prf production by MMC as determined by flow cytometry analysis of gated neu+ MMC in the co-culture (not shown). In addition, MDSC did not suppress production of GrB or expression of the CD69 early activation marker in the expanded T cells (not shown). PBMC from naive FVBN202 mice that was depleted of Gr1+ cells had no suppressive effect or supportive effect on tumor-reactive T cells (data not shown). These data suggest that MDSC did not inhibit anti-tumor responses of the T cells expanded with the sequential gamma-chain cytokine regimen. We next determined whether MDSC could inhibit cytotoxicity of these T cells against MMC tumor cells in vitro. Expanded cells were cultured with viable neu+ MMC (10:1 ratio) in the presence of absence of MDSC (2:1 ratio). Control MMC cells were cultured with medium alone. As shown in FIG. 4C, expanded cells induced apoptosis in MMC cells in a 2-day culture, and the presence of MDSC did not alter the cytotoxic function of the tumor-reactive cells.

Presence of Non-T Cells in the Ex Vivo Expanded Cells Overcomes MDSC and Enhances T Cell Responses to MMC Cells The ex vivo expanded cells showed a significantly reduced proportion of CD4–CD8– cells compared to that of freshly isolated splenocytes (D 6: 20% vs. D 0: 57%, p=0.0001, FIG. 5A). The expanded cells contained 17-20% CD4–CD8– cells. As shown in FIG. 5B, gated CD4–CD8– cells contained a significantly higher proportion of CD3+ cells in the expanded cells compared to freshly isolated cells (D 6: 60.8% vs. D 0: 5.5%, p=0.002). We sought to determine the cellular composition of these CD4–CD8– cells. CD49b is a common marker for NK cells, NK T cells and IFN-γ producing killer DC (IKDC) (24). As shown in FIG. 5C, NK T cells (CD49b+ CD3+) and NK cells (CD49b+CD3–) showed significant increases in the expanded CD4–CD8– cells. The proportion of IKDC (CD49b+CD3–B220+) in the gated CD3–CD11b+ cells was also significantly increased after the expansion (FIG. 5D, p=0.001). The CD3+CD49+ NK T cells and CD3– CD49b+ NK cells showed higher expression of the activation marker CD25 after a 6-day expansion (D 6) compared to freshly isolated cells (D 0) (not shown). The expanded CD3+ non-T cells (NK T cells) showed higher viability compared to the expanded CD3– non-T cells (NK cells and IKDC) (FIG. 5E: 71.9% vs. 37.5% on day 6, p=0.004).

In order to determine whether the presence of non-T cells renders the tumor-reactive T cells resistant to MDSC, in vitro and in vivo studies were performed on the sorted cells. The ex vivo expanded cells were sorted into CD4+ plus CD8+ T cells and CD4–CD8– non-T cells. Sorted cells were then cultured for 24 hs in the presence or absence of irradiated MMC (10:1 ratio of expanded cells to MMC) to show their reactivity with MMC in the presence or absence of MDSC (2:1 ratio of expanded cells to MDSC). Supernatants were collected and subjected to IFN-γ ELISA. As shown in FIG. 5F, MDSC induced secretion of IFN-γ by CD4–CD8– non-T cells in the presence of MMC but not in CD4+ plus CD8+ T cells (p=0.031). Lower amounts of IFN-γ were secreted by sorted CD4+ plus CD8+ T cells compared to unsorted cells ($10^7$ pg/ml in FIG. 5F compared to 2642 pg/ml in FIG. 4A). This suggests that the presence of non-T cells boosts the tumor-reactivity of T cells. In addition, the presence of MDSC significantly increased MMC-induced IFN-γ production by non-T cells (p=0.006). However, CD4+ plus CD8+ T cells in the absence of non-T cells lost their ability to secrete MMC-specific IFN-γ while MDSC were present. This suggests that MDSC-stimulated, MMC-activated non-T cells render T cells resistant to MDSC. ACT with sorted T cells or non-T cells failed to protect FVBN202 mice from challenge with MMC cells (FIG. 5G). Since IL-12 induces the expression of IFN-γ by NK cells and T cells, we sought to determine whether CD4–CD8–CD49b+ cells produce IL-12 in the presence of MMC and MDSC, resulting in the induction of enhanced IFN-γ production by T cells. No IL-12 production was detected in non-T cells or T cells (data not shown).

Radiation Therapy of Tumor-Bearing Mice Prior to the Isolation of Donor T Cells Results in Failure of the Expanded T Cells to Generate Objective Responses Upon ACT Despite Sustained Anti-Tumor Responses of the T Cells In Vitro Cancer patients who participate in clinical trials of ACT have usually received conventional therapies, often including radiation therapy. Therefore, it is important to determine whether tumor-primed T cells that were isolated following radiation therapy can also be expanded, and can generate objective responses against the tumors following ACT. In order to test this. FVBN202 mice were inoculated with MMC cells and as soon as tumors reached 75-150 mm$^3$, animals received three doses of local radiation therapy to the tumor site (5 Gy) in a 3-day interval. Animals were then sacrificed one week after the last radiation treatment and their splenocytes subjected to B/I activation and a 6-day expansion with sequential common gamma-chain cytokines. The frequency of freshly isolated T cells was significantly lower after radiation therapy (FIG. 6A) compared to that without radiation therapy (FIG. 1A) (CD8+ T cells, p=0.002; CD4+ T cells, p=0.0002). However, radiation therapy did not alter the ability of T cells to grow after B/I activation, such that after six days in culture, the cells showed similar rates of expansion compared to those from mice that did not receive any radiation (FIG. 6A and FIG. 1A). The frequency of apoptotic T cells did not increase during the ex vivo expansion (not shown). However, expanded T cells from mice subjected to radiation failed to increase CD127 (not shown), and increased expression of CD122 was evident only in CD8+ T cells (not shown).

In order to determine the tumor-reactivity of the expanded T cells from mice whose tumors had been irradiated, in vitro studies were performed. As shown in FIG. 6B, freshly isolated T cells (D 0) and ex vivo expanded cells (D 6) failed to produce significant amounts of IFN-γ upon MMC stimulation. However, the addition of MDSC resulted in the induction of IFN-γ by the expanded T cells (FIG. 6B). The expanded cells were also comprised of 19.2% non-T cells (not shown). Interestingly, the proportion of Prf+ T cells in the expanded T cells (D 6) was markedly higher in this group that had received prior radiation therapy (RAD) compared to T cells that were isolated from donors with no prior radiation therapy (NT) (FIG. 6C). Expanded CD8+ T cells were highly positive for the expression of CD69 and GrB (not shown). Importantly, lack of IFN-γ production by the expanded T cells did not alter the ability of these cells to kill neu+ MMC cells in vitro such that viability (Annexin V–/PI–) of MMC was reduced from 64.64% to 12.35% in the presence of the expanded T cells (FIG. 6D). In addition, expanded T cells were able to kill neu+ MMC cells even in the presence of MDSC in vitro, as shown by a reduced viability from 64.64% to 12.35% and 8.46% (FIG. 6D).

Results of in vivo studies presented in FIG. 3 suggest a correlation between phenotypic distribution of T cells and objective responses following ACT such that high proportions of TCM were associated with the rejection of primary and recall tumor challenge. Therefore, we performed phenotype analysis of post-radiation T cells before proceeding with ACT. As shown in FIG. 6E, phenotypic distribution of CD8+ and CD4+ T cells was different from those isolated from animals with no prior radiation therapy (FIG. 3A). Freshly isolated CD8+ T cells (D 0) were mainly of TCM and TN phenotypes whereas CD4+ T cells contained TE and TEM (FIG. 6E). After six days of ex vivo expansion, CD8+ T cells were enriched for TE whereas CD4+ T cells contained TE and TEM phenotypes. After a 6-day expansion, CD8+ TCM and TN phenotypes had almost disappeared. An increased proportion of CD8+ TE cells may account for the in vitro efficacy of the expanded T cells against MMC cells, though anti-tumor efficacy in vivo may require tumor-specific TCM cells. To test this possibility ACT studies were performed as described above. As shown in FIG. 6F, ACT using the ex vivo expanded cells from mice whose tumors had been irradiated showed minimal tumor inhibitory effects compared to the control group. The rate of tumor growth was the same in the two groups ($p<0.21$), though the change from day to day was significant ($p<0.0001$).

HER-2/neu-Specific T Cells can be Expanded from PBMC of a Patient with Breast Cancer Splenocytes isolated from tumor-bearing mice with no radiation therapy were effective against the neu+ MMC cells despite the lack of splenic tumor metastasis. This suggests that tumor-reactive T cells may be present in the circulation. To test this, PBMC were collected from a breast cancer patient after Ficoll-Paque gradient centrifugation of blood and split into two fractions. Adherent cells were selected by 2 hs culture and used for generating autologous DCs by a 6-day culture in the presence of GM-CSF and IL-4, as described elsewhere (25). Non-adherent cells were split into two fractions. One fraction was maintained in complete RPMI1640 supplemented with 10% FBS and IL-2 (40 U/ml/$10^6$ cells) at 37° C./5% $CO_2$ for 6 days (IL-2 maintained cells). The remaining cells were subjected to B/I activation and expansion with the common gamma-chain cytokines (expanded cells with IL-7, IL-15, IL-2). Viability of the T cells (Annexin V-) after a 6-day culture or ex vivo expansion was greater than 85% (data not shown). Cells were then co-cultured with autologous DCs in the presence or absence of recombinant HER-2/neu protein for 24 hs. In order to rule out non-specific IFN-γ production by CD4+ T cells as a result of low endotoxin levels in the HER-2/neu recombinant protein, we pulsed control wells with LPS. As shown in FIG. 7A-B, compared to IL-2 maintained T cells, the B/I-activated and expanded cells produced significantly higher amounts of IFN-γ when stimulated with HER-2/neu (average 8600 vs. 32500 pg/ml, p=0.001). Flow cytometry analysis of IL-2 maintained and ex vivo expanded T cells determined that both CD8+ T cells and CD4+ T cells were sources of HER-2/neu-stimulated IFN-γ production (FIG. 7C).

Discussion

Development of an ex vivo protocol that can expand highly efficient populations of tumor-reactive immune cells, which include cells of the adaptive and innate immune systems, may be the key to successful ACT in the breast cancer model. Others have reported that rejection of mammary carcinoma in HER-2/neu transgenic mice depends on the stimulation of both innate and adaptive immunity (25). In addition, NK T cells have been shown to be involved in secondary anti-tumor T cell responses (26).

Data presented herein demonstrated that activation of tumor-primed lymphoid cells with B/I followed by ex vivo expansion with sequential common gamma-chain cytokines can activate and expand tumor-reactive T cells and non-T cells including NK T cells, NK cells and IKDC. A number of the cytokine combinations (7, 21, 22) were tested and it was found that IL-7+IL-15 followed by IL-2 was the best sequence for the expansion of the most effective cells. The presence of activated non-T cells in the expanded cells was critical not only for the in vivo anti-tumor efficacy of T cells but also for their resistance to MDSC. The absence of such activated non-T cells in freshly isolated splenocytes or depletion of these non-T cells in the expanded cells resulted in susceptibility to MDSC-induced suppression of tumor-reactive T cells. Neither tumor-reactive T cells nor these non-T cells alone were able to protect FVBN202 mice against tumor challenge when they were used separately in ACT. Since the viability of NK cells was very low (37.5%) as opposed to the high viability (72%) of NK T cells, it is likely that NK T cells are the key component of the supportive cells. These findings are consistent with recent reports showing that cells of the innate and adaptive immune system work together to produce objective responses against tumors (25, 26). These results also showed that MDSC can further activate the ex vivo expanded non-T cells, as shown by an increased CD25 expression, thereby enhancing the supportive function of non-T cells for tumor-reactive T cells. This is the first report showing a cellular mechanism by which T cells may become resistant to MDSC. Because of the T cell inhibitory role of MDSC in a variety of cancers, the proposed protocol could be applicable to a variety of carcinomas. Although the presence of T cells and cells of the innate immune system were critical for anti-tumor efficacy of the immune response, long-term protection against the tumor depended on the presence of TCM cells. These data suggest that B/I activation and ex vivo expansion with sequential common gamma-chain cytokines may have improved the quality of neu-specific cells for tumor rejection, and it was not just because of an increase in frequency of neu-specific T cells. For instance, freshly isolated T cells from tumor-bearing but not from tumor-free FVBN202 mice produced IFN-γ upon stimulation with MMC in vitro; yet such increased frequency of endogenous neu-specific T cells did not induce tumor rejection in donor mice. In addition, ACT with an increased numbers of freshly isolated T cells derived from tumor-bearing donors ($2 \times 10^9$ cells/mouse) did not protect mice against tumor challenge (data not shown). These data suggest that an increase in neu-specific T cells without ex vivo expansion/differentiation using the proposed protocol cannot provide protection against the tumor. Whereas T cells from non-irradiated and post-radiation donors showed comparable levels of anti-tumor efficacy in vitro (FIG. 6D), T cells obtained from non-irradiated donors provided long-term memory responses against recall tumor challenge in vivo, likely because of the phenotypic distribution of T cells toward TCM cells. Local radiation therapy of the tumors in donor mice altered the phenotypic distribution of freshly isolated T cells as well as the capacity of T cells to differentiate into TCM cells during the ex vivo expansion. These data suggest that CD8+ TE and TEM cells may be more susceptible to radiation therapy than previously established TCM cells, as has been reported by others (27). These data suggest that local radiation therapy could alter the differentiation of tumor-reactive CD8+ TE and TEM cells toward TCM cells. However, local radiation therapy of primary tumors was performed whereas breast cancer patients usually receive radiation therapy after surgery to destroy residual microscopic disease. Also, patients with advanced breast cancer have undergone multiple radiation treatments followed by a period of recovery prior to ACT. These scenarios are somewhat different from the treatment protocol that used in this study. In order for T cell to be effective for ACT it was necessary to isolate T cells from tumor-bearing animals. Therefore, radiation therapy was performed on primary tumors. Application of the proposed approach may be limited to patients with early stage breast cancer (stage I-III), provided that PBMC are harvested and cryopreserved prior to radiation therapy for ACT in the future.

The importance of TCM against cancer has also been reported by others (4). These data showing a greater anti-tumor efficacy of ACT in association with the presence of TCM are consistent with other reports showing that effector cells derived from TCM rather than TEM possess greater ability to survive and establish immunologic memory following infusion (28). However, naïve T cells have been reported to convey more anti-tumor activity than memory cells (28). Such contradictory results may be due to the use of a mouse model harboring a transgenic T cell receptor for gp100 tumor antigen, which is different from the FVN202 mouse model of spontaneous breast carcinoma with no transgenic TcR against the tumor antigen.

IL-7 has been shown to support viability and homeostatic proliferation of T cells and enhance NK cell function (29). IL-15 supports differentiation of memory T cells and activation of quiescent NK cells more efficiently than IL-2 (30). IL-2 is T cell growth factor and is also involved in NK cell activation and proliferation. Therefore, culture of tumor-primed T cells initially with IL-7+IL-15 followed by IL-2 can support differentiation of T cells as well as non-T cells. The presence of non-T cells in this model appears to be critical for rendering T cells resistant to MDSC, regardless of whether T cells were obtained before or after radiation therapy. A similar observation has been made in mice and humans with hematologic malignancies undergoing allogeneic stem cell transplantation. In the animal model, depletion of donor NK cells abrogated anti-leukemia effects of donor T cells (31). In humans, early donor derived NK cell recovery has been shown to be associated with a lower relapse risk in the non-myeloablative setting in the recipients of T cell replete allografts (32). Earlier observations in the same clinical model had demonstrated a significant impact of NK cell dose in the graft on day 28 T cell chimerism (33). Similarly a trend towards a higher level donor T cell chimerism at 12 weeks post transplant, in patients with superior NK cell recovery at 4 weeks has been observed (unpublished data). Together these data provide intriguing evidence of T cell-NK cell interactions in the clinical transplant setting and suggesting interdependence between innate and adaptive immunity.

Altogether, these data suggest that lymph nodes (11) or PBMC of breast cancer patients are a source of tumor-reactive immune cells for ex vivo expansion and use in ACT, provided that immune cells are obtained prior to radiation therapy and expanded with the sequential common gamma-chain cytokines. Expanded T cells and non-T cells obtained prior to radiation therapy can be cryopreserved and used for experimental ACT protocols after the completion of conventional therapies in an attempt to eliminate residual disease and prevent tumor relapse.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

1) Yee, C., J. et. al. 2002. Proc. Natl. Acad. Sci. U.S.A. 99:16168-16173.
2) Dudley, M. E., et. al. 2002. Science 298:850-854.
3) Johnson, L. A., et. al. 2009. Blood 114:535-546.
4) Berger, C., et. al. 2008. J. Clin. Invest. 118:294-305.
5) Liu, S., et. al. 2006. J. Immunother. 29:284-293.
6) Bernhard, H., et. al. 2008. Cancer Immunol. Immunother. 57:271-280.
7) Morales, J. K., et. al. 2009. Cancer Immunol. Immunother. 58:941-953.
8) Ho, W. Y., et. al. 2002. J. Clin. Invest. 110:1415-1417.
9) Diaz-Montero, C. M., et. al. 2009. Cancer Immunol. Immunother. 58:49-59.
10) Blankenstein, T. 2005. Curr. Opin. Immunol. 17:180-186.
11) Bear, H. D., et. al. 2001. Cancer Immunol. Immunother. 50:269-274.
12) Kazanietz, M. G., et. al. 1994. Mol. Pharmacol. 46:374-379.
13) Chatila, T., et. al. 1989. 143:1283-1289.
14) Ariza, M. E., et. al. 2010. J. Biol. Chem. 286:24-34.
15) Guy, C. T., et. al. 1992. Proc. Natl. Acad. Sci. U.S.A. 89:10578-10582.
16) Kmieciak, M., et. al. 2008. Cancer Immunol. Immunother. 57:1391-1398.
17) Kmieciak, M., et. al. 2009. J. Transl. Med. 7:89.
18) Worschech, A., et. al. 2008. Cancer Res. 68:2436-2446.
19) Morales, J. K., et. al. 2010. Breast Cancer Res. Treat. 123:39-49.
20) Le, H. K, et. al. 2009. Int. Immunopharmacol. 9:900-909.
21) Cha, E., et. al. 2010. Breast Cancer Res. Treat. 122:359-369.
22) Le, H. K., et. al. 2009. Cancer Immunol. Immunother. 58:1565-1576.
23) Manjili, M. H., et. al. 2002. Cancer Res. 62:1737-1742.
24) Terme, M., et. al. 2009. Cancer Res. 69:6590-6597.
25) Spadaro, M., et. al. 2005. Clin. Cancer Res. 11:1941-1952.
26) Hong, C., et. al. 2009. Cancer Res. 69:4301-4308.
27) De Ruysscher, D., et. al. 1992. Eur. J. Cancer 28A:1729-1734.
28) Hinrichs, C. S., et. al. 2009. Proc. Natl. Acad. Sci. U.S.A. 106:17469-17474.
29) Tan, J, T., et. al. 2001. Proc. Natl. Acad. Sci. U.S.A. 98:8732-8737.
30) Pillet, A. H., et. al. 2009. J. Immunol. 182:6267-6277.
31) De Somer, L., et. al. 2011. Haematologica 2011; January 12 [Epub ahead of print]
32) Baron, F., et. al. 2009. Biol. Blood Marrow Transplant 15:580-588.
33) Panse, J. P., et. al. 2005. Br. J. Haematol. 128:659-667.

We claim:

1. A method of producing resistant autologous immune cells, comprising the steps of
exposing immune cells obtained from a patient a breast cancer patient or a melanoma patient to bryostatin and ionomycin (B/I); then
exposing said immune cells to a combination of IL-7 and IL-15; then
removing said immune cells from exposure to said combination of IL-7 and IL-15; and exposing said immune cells to IL-2;
thereby producing autologous immune cells that, in the aggregate, are resistant to the effects of myeloid-derived suppressor cells (MDSCs).

2. The method of claim 1, wherein said step of exposing said immune cells to said combination of IL-7 and IL-15 is carried out for 24 hours.

3. The method of claim 1, wherein said step of exposing said immune cells to IL-2 includes
adding IL-2 to said immune cells after said step of removing said combination of IL-7 and IL-15.

4. The method of claim 1, wherein said immune cells include innate and adaptive immune cells.

5. The method of claim 1, wherein said immune cells include tumor-primed T cells.

6. The method of claim 1, wherein said immune cells are peripheral blood mononuclear cells (PBMCs).

7. The method of claim 1, wherein said resistant autologous immune cells include T cells, natural killer (NK) cells, NKT cells and IFN-γ producing killer dendritic cells (IKDC).

8. The method of claim 7, wherein said T cells include memory T cells (TCMs) and effector T cells (TEs).

9. The method of claim 1, wherein said patient has not received radiation therapy for at least one month prior to a time when said immune cells are obtained from said patient.

10. The method of claim 1, wherein said patient is a breast cancer patient.

11. The method of claim 1, wherein said step of exposing said immune cells to said IL-2 includes the steps of
exposing said immune cells to said combination of IL-7 and IL-15 for 24 hours, and after said 24 hours, exposing said immune cells to IL-2 in the presence of said combination of IL-7 and IL-15; then
exposing said immune cells to IL-2 alone.

12. The method of claim 9, wherein said patient is a breast cancer patient.

13. The method of claim 1, wherein said removing step includes washing said immune cells.

* * * * *